US005868661A

United States Patent [19]

Williams et al.

[11] Patent Number: 5,868,661

[45] Date of Patent: Feb. 9, 1999

[54] ARTIFICIAL INSEMINATION APPARATUS

[75] Inventors: Stanley Williams, Ames, Iowa; Craig C. Martin, Clayton, N.C.; Bert Wright, Winterville, N.C.; Robert C. Lynch; Daniel C. Fuccella, both of Cary, N.C.

[73] Assignee: Artificial Insemination Technologies LLC, Holly Springs, N.C.

[21] Appl. No.: 918,458

[22] Filed: Aug. 26, 1997

[51] Int. Cl.[6] .......... A61M 5/00

[52] U.S. Cl. .......... 600/35

[58] Field of Search .......... 600/33–35; 604/27, 604/30, 36, 37, 41–44, 48, 54, 55, 96–104; 119/7; 239/16, 17, 24, 33

[56] References Cited

U.S. PATENT DOCUMENTS 5,536,243 7/1996 Jeyendran .

OTHER PUBLICATIONS

Pork Industry Handbook PIH–64, "Artificial Insemination in Swine", Diehl, et al, pp. 1–6, Jan. 1996.

*Primary Examiner*—John P. Lacyk

*Assistant Examiner*—Samuel Gilbert

*Attorney, Agent, or Firm*—Steven J. Hultquist; William A. Barrett

[57] ABSTRACT

An artificial insemination apparatus for insertion into a cervix of a sow, including a tubular passage member which is helically coiled at a distal end. The helically coiled distal end terminates in an open tip including an opening communicating with a bore of the tubing. The helically coiled distal end is inserted into and is secured by the muscular folds in the cervix, and semen is transmitted therethrough.

15 Claims, 2 Drawing Sheets

ARTIFICIAL INSEMINATION APPARATUS

BACKGROUND OF THE INVENTION

1. Field of the Invention

This invention relates to artificial insemination and, more particularly, to an apparatus for artificially inseminating livestock.

2. Description of the Related Art

Artificial insemination (AI) is an increasingly valuable technique and management practice for the pork producer. AI allows the pork producer widespread use and dissemination of outstanding boars and increases the number of offspring from the best boars. AI is invaluable for breeding under various environmental and managerial conditions, and allows the pork producer to accelerate the introduction of new genetic material. AI also reduces the spread of sexually-transmitted diseases within the stock and prevents injuries common in natural service.

Pork producers and researchers have attempted to mimic the anatomy of a boar to make artificial insemination successful for the pork industry. In natural service the boar's penis has developed spiral glands to engage the muscular folds of the sow's cervix. This specialization locks the spiral tip of the penis in the folds of the cervix. This locking action during coitus ensures the bulk of the semen is transmitted into the uterus of the sow. The artificial insemination rods currently used by pork producers include an overmolded tip portion designed to simulate the spiral tip of the boar's penis. The insemination rod is inserted into the cervix and manipulated to simulate the natural locking action. Boar semen is then passed through the hollow rod and into the uterus.

Though artificial insemination is vital to the pork industry, insemination rods have changed little over the years despite persistent disadvantages with the overmolded tip portion. The tip portion has heretofore been available in two primary configurations, i) an elongate tip with a spiral flange or ii) a bulbous tip with a circumferential groove. Although each is designed to mimic the tip of the boar penis and lock the rod in the muscular folds of the cervix, neither configuration provides a secure interlock for the transmission of semen. Since the overmolded tip portion can separate from the hollow tube and cause blockage of the cervix, safe removal of the overmolded insemination rod is of a great concern.

Several other problems are associated with the overmolded insemination rod designs. Since the rod is often rotated to interlock within the cervix, molded material flash or sharp flange comers can cause damage to the interior wall tissue of the cervix. The material compound of the overmolded tip also presents a tradeoff between reusability and interior wall tissue damage. The molding operation used to produce the overmolded tip also unnecessarily increases the cost of the insemination rods.

There is, accordingly, a need in the art for an insemination rod design which improves securability in the cervix of a sow, which is reliably removed from the cervix, which reduces damage to the interior wall of the cervix, and which is cost effective to manufacture.

SUMMARY OF THE INVENTION

The aforementioned problems are resolved by an artificial insemination apparatus for insertion into a cervix of a sow, including a tubular passage member which is helically coiled at a distal end. The helically coiled distal end terminates in an open tip including an opening communicating with a bore of the tubing. The helically coiled distal end is inserted into and is secured by the muscular folds in the cervix, and semen is transmitted therethrough.

The invention is more fully disclosed hereafter with regard to various preferred and illustration aspects, features and embodiments

BRIEF DESCRIPTION OF THE DRAWINGS

These and other features, aspects, and advantages of the present invention will become better understood when the following detailed description is read with reference to the accompanying drawings wherein.

DETAILED DESCRIPTION OF THE INVENTION, AND PREFERRED EMBODIMENTS THEREOF

Although described hereinafter in primary reference to use as an artificial insemination apparatus for swine, the apparatus of the present invention is not thus limited in species, yet, may be used for artificial insemination in the cow, ewe, doe, mare, and other mammals.

Figure 1:
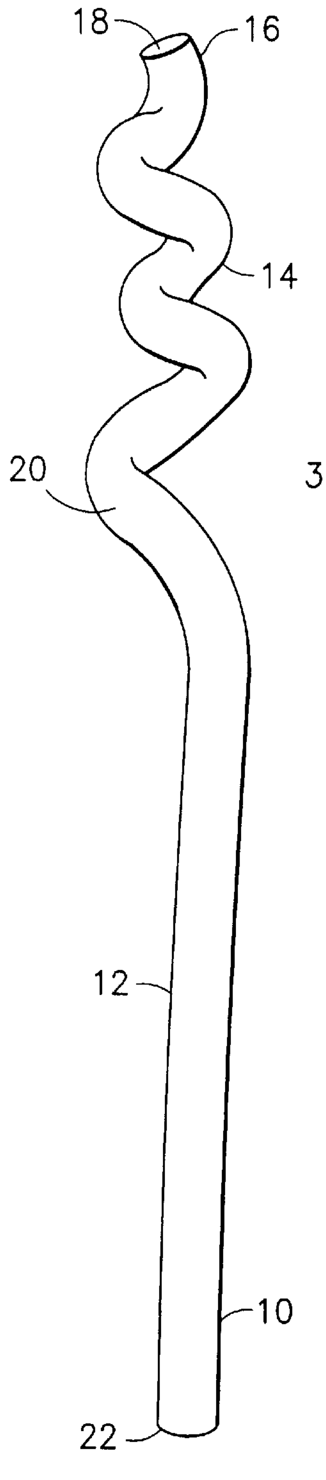
FIG. 1 is a perspective view of an artificial insemination apparatus according to one embodiment of the present invention.

FIG. 1 is a perspective view of an artificial insemination apparatus 10 according to one embodiment of the present invention. The artificial insemination apparatus includes a tubular passage member 12 defining a longitudinal axis and bounded by an enclosing wall to define a cross-section of the tubular passage transverse to the longitudinal axis. A distal end 14 of tubular member 12 is helically coiled to conform to the muscular folds of the sow cervix.

The distal end 14 of the apparatus 10 tapers and terminates in an open tip 16. The open tip includes an opening 18 in fluid communication with a bore 20 of the tubular passage member 12. Semen is introduced into bore 20 at proximal end 22 and is flowed through the apparatus for discharge at opening 18.

Figure 2:
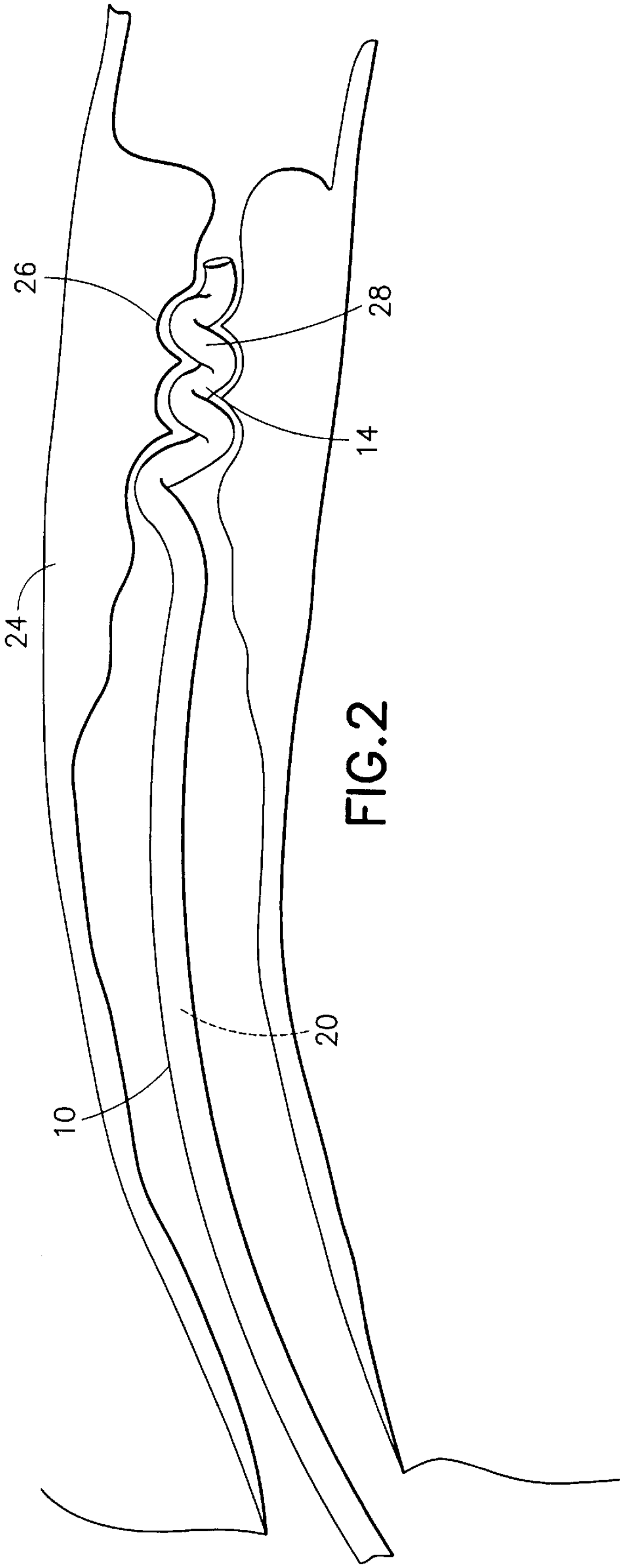
FIG. 2 is a sectional diagrammatic representation of engagement between the apparatus of FIG. 1 and the muscular folds of a sow cervix.

FIG. 2 is a sectional diagrammatic representation of engagement between the apparatus of FIG. 1 and the muscular folds of a sow cervix. The artificial insemination apparatus 10 is inserted as shown into the cervix 24 of the sow. The muscular folds 26 contract during insemination and secure distal end 14. The helical design of the distal end allows the musculature of the cervix to fully contract into the spaces between each coil 28. The deep penetration of the muscular folds into the spaces between each coil improves the securability of apparatus 10 and ensures the entire volume of semen flowed through bore 20 is deposited into the uterus.

The artificial insemination apparatus of FIGS. 1 and 2 is less injurious to the cervix. Since the distal end 14 of tubular member 10 is helically coiled, there is no overmolded tip portion. The lack of an overmolded tip reduces the danger of damaging the interior of the cervix from molded material flash or sharp flange comers. There is also no danger of the overmolded tip separating from the hollow tube and causing blockage of the cervix.

The artificial insemination apparatus of FIGS. 1 and 2 is also cost effective to manufacture. The tubular passage member 10 has been produced by extrusion, and the helically coiled distal end is formed using a conical mandrel while in a heated state. Other methods of forming the helically coiled distal end include a die at the exit of the extrusion process, or a bend fixture at the exit of the extrusion process. The artificial insemination apparatus has been produced using rigid polyvinyl chloride material with appropriate melt characteristics for bending. Other materials include more traditional high density polyethylene, low density polyethylene, and low density polypropylene compounds.

The specific size of the apparatus of FIGS. 1 and 2 may be simply determined without undue experimentation for a given species by varying the size of the apparatus to the natural conformation of the species to be inseminated. If, for example, a sow is to be artificially inseminated, the apparatus of FIGS. 1 and 2 would have an overall length of about 20 inches. The outer diameter of the helically coiled distal end would be about 0.7 inches and would taper to about 0.56 inches. Each coil of the helically coiled distal end would be spaced by about 0.7 inches. The tubular passage member would have an outer diameter of about 0.27 inches and an inner diameter of about 0.187 inches.

Figure 3:
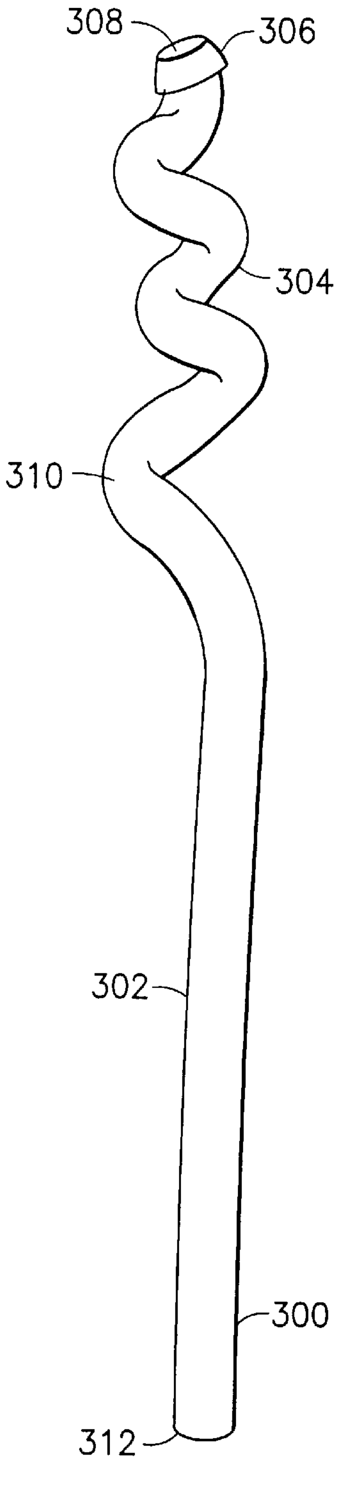
FIG. 3 is a perspective view of an artificial insemination apparatus according to another embodiment of the present invention.

FIG. 3 is a perspective view of an artificial insemination apparatus 300 according to another embodiment of the present invention. This embodiment includes tubular passage member 302 with distal end 304 conically helically coiled to conform to the muscular folds of the sow cervix. Distal end 304 terminates in mushroom-like tip 306. Mushroom-like tip includes an opening 308 in fluid communication with a bore 310 of the tubular passage member 302. Semen is introduced into bore 310 at proximal end 312 and is flowed through the apparatus for discharge at opening 308. The mushroom conformation of tip 306 helps prevent the tip from injuring the cervix interior during insertion and removal of the apparatus. Those skilled in the art will recognize various other tip conformations are possible to aid insertion and removal of the apparatus from the cervix, such as a bulbous conformation.

Figure 4:
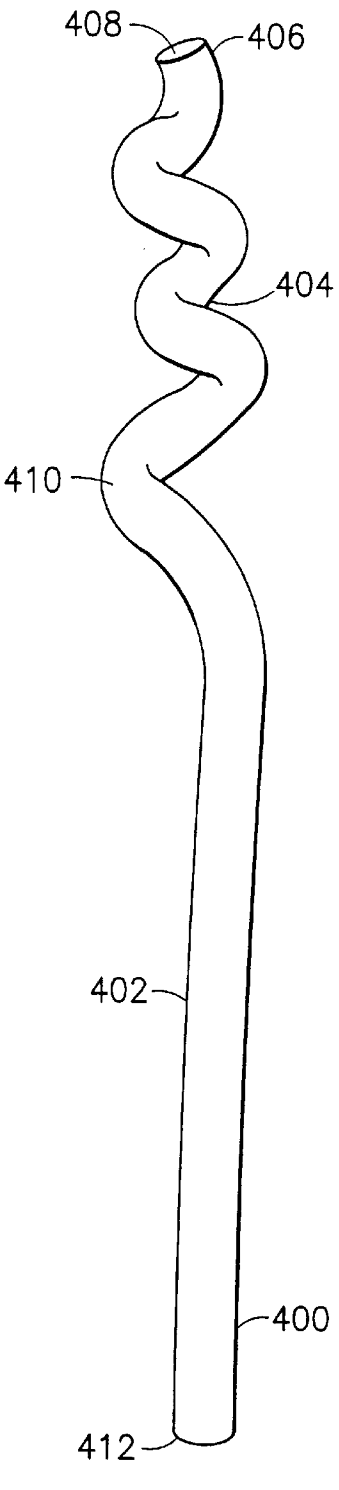
FIG. 4 is a perspective view of an artificial insemination apparatus according to still another embodiment of the present invention.

Although the distal end has heretofore been described and shown in the shape of a conical helix, FIG. 4 is a perspective view of an artificial insemination apparatus 400 according to another embodiment of the present invention. This embodiment includes tubular passage member 402 with distal end 404 cylindrically helically coiled. Each coil of the cylindrically helically coiled distal end has an outer diameter, for the insemination of a sow, of about 0.7 inches, and each coil is spaced by about 0.7 inches. Distal end 404 terminates in open tip 406. Open tip includes an opening 408 in fluid communication with a bore 410 of the tubular passage member 402. Semen is introduced into bore 410 at proximal end 412 and is flowed through the apparatus for discharge at opening 408. Open tip 406 could alternatively have the mushroom conformation shown in FIG. 3.

While the invention has been described herein with reference to specific embodiments and features, it will be appreciated the utility of the invention is not thus limited, yet, encompasses other variations, modifications, and alternative embodiments and, accordingly, the invention is, therefore, to be broadly construed as comprehending all such alternative variations, modifications, and other embodiments within its spirit and scope.

What is claimed is:

1. An artificial insemination apparatus for insertion into a cervix of an animal comprising a virgate tubular passage member through which semen can be transported, which is helically coiled at a distal end and terminates in an open tip including an opening communicating with a bore of the tubing, wherein the helically coiled end is adapted to be inserted into and secured by muscular folds in the cervix.

2. An artificial insemination apparatus according to claim 1, wherein said tubular passage member is conically helically coiled at the distal end.

3. An artificial insemination apparatus according to claim 1, wherein said open tip includes a mushroom conformation to aid insertion into the cervix.

4. An artificial insemination apparatus according to claim 1, wherein said tubular passage member is cylindrically helically coiled at the distal end.

5. An artificial insemination apparatus according to claim 1, wherein said apparatus is constructed of polyvinyl chloride material.

6. An artificial insemination apparatus according to claim 1, wherein said apparatus is constructed of extruded polyvinyl chloride material.

7. An artificial insemination apparatus according to claim 1, wherein said apparatus has a length of about 20 inches.

8. An artificial insemination apparatus according to claim 1, wherein the virgate tubular passage member is of sufficient length that when the helically coiled end is inserted into the cervix, the virgate member extends outside the animal's body.

9. An artificial insemination apparatus for insertion into a cervix, comprising:

a) a virgate tubular passage member through which semen can be transported, which is helically coiled at a distal end and terminates in an open tip including an opening communicating with a bore of the tubing;

b) the tubular passage member having an outer diameter of about 0.27 inches;

c) the helically coiled distal end having an outer diameter of about 0.7 inches, and a spacing between each coil of about 0.7 inches;

wherein the helically coiled end is adapted to be inserted into and secured by muscular folds in the cervix.

10. An artificial insemination apparatus according to claim 9, wherein said apparatus has a length of about 20 inches.

11. An artificial insemination apparatus according to claim 9, wherein said apparatus is constructed of polyvinyl chloride material.

12. An artificial insemination apparatus according to claim 9, wherein said tubular passage member is conically helically coiled at the distal end.

13. An artificial insemination apparatus for insertion into a cervix of an animal comprising a virgate tubular member in fluid communication and terminating with a helically coiled tubular member wherein the virgate tubular member is of sufficient length that when the helically coiled tubular member is placed in the cervix, the virgate tubular member extends outside the animal's body.

14. The artificial insemination apparatus of claim 13 wherein each coil of the helically coiled member is spaced from a next successive coil by about 0.7 inches.

15. The artificial insemination apparatus of claim 13 wherein the helically coiled member has an outer diameter of about 0.7 inches.

* * * * *

UNITED STATES PATENT AND TRADEMARK OFFICE
CERTIFICATE OF CORRECTION

PATENT NO : 5,868,661

DATED : February 9, 1999

INVENTOR(S) : Williams et al.

It is certified that error appears in the above-identified patent and that said Letters Patent is hereby corrected as shown below:

Column 1, Line 50, change "comers" to –corners--
Column 2, Line 67, change "comers" to --corners--

Signed and Sealed this

Twenty-seventh Day of July, 1999

Attest:

Q. TODD DICKINSON

*Attesting Officer* *Acting Commissioner of Patents and Trademarks*